United States Patent
Yelle

(10) Patent No.: US 6,352,984 B1
(45) Date of Patent: Mar. 5, 2002

(54) OLANZAPINE-N-OXIDE COMPOSITIONS AND METHODS

(75) Inventor: William E. Yelle, Littleton, MA (US)

(73) Assignee: Sepracor Inc., Marlborough, MA (US)

(*) Notice: Subject to any disclaimer, the term of this patent is extended or adjusted under 35 U.S.C. 154(b) by 0 days.

(21) Appl. No.: 09/632,584

(22) Filed: Aug. 7, 2000

Related U.S. Application Data

(62) Division of application No. 09/444,159, filed on Nov. 22, 1999, now Pat. No. 6,121,259.
(60) Provisional application No. 60/109,551, filed on Nov. 23, 1998.
(51) Int. Cl.[7] ................................................ A61K 31/55
(52) U.S. Cl. ........................ 514/220; 514/810; 514/811; 514/812; 424/451; 424/464
(58) Field of Search .................................... 514/220, 810, 514/811, 812; 424/451, 464

(56) References Cited

PUBLICATIONS

Calligaro et al, "The synthesis and biological activity of some known and putative metabolites of the atypcial antipsychotic agent olanzapine (LY170053)", Biorg. Med. Chem. Lett., vol. 7, pp. 25–30, Apr. 1997.*

Ring et al, "Identification of the human cytochromes P450 responsible for the in vitro formation of the major oxidative metabolites of the antipsychotic agent olanzapine", J. Pharm. Exp. Ther., vol. 276, pp. 658–666, Apr. 1996.*

* cited by examiner

Primary Examiner—Frederick Krass
(74) Attorney, Agent, or Firm—Heslin Rothenberg Farley & Mesiti P.C.

(57) ABSTRACT

Methods and compositions are disclosed utilizing olanzapine-N-oxide for the treatment of psychosis in humans. Olanzapine-N-oxide exhibits a lessened liability toward drug-drug interactions than olanzapine and a more predictable dosing regimen than olanzapine. Olanzapine-N-oxide is also useful for the treatment of acute mania, mild anxiety states, anxiety disorders, schizophrenia, bipolar disorder, attention deficit hyperactivity disorder, autistic disorder, excessive aggression, substance abuse, depressive signs and symptoms, tic disorder, functional bowel disorder and fungal dermatitis.

3 Claims, No Drawings

OLANZAPINE-N-OXIDE COMPOSITIONS AND METHODS

This is a divisional application of U.S. application Ser. No. 09/444,159, filed Nov. 22, 1999, now U.S. Pat. No. 6,121,259. This application also claims benefit of U.S. Provisional Appln. No. 60/109,551, filed Nov. 23, 1998.

FIELD OF THE INVENTION

The invention relates to methods of treating psychosis, acute mania, mild anxiety states, schizophrenia, bipolar disorder, autistic disorder, excessive aggression, substance abuse, depressive signs and symptoms, tic disorder, functional bowel disorder and fungal dermatitis.

BACKGROUND OF THE INVENTION

Olanzapine I is an orally active, potent, antipsychotic agent.

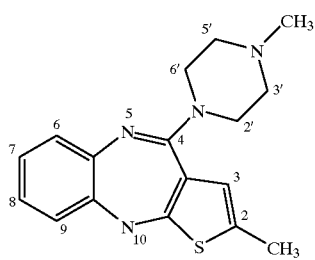

I

It is commercially available as Zyprexa® from Eli Lilly Co. The antipsychotic effect of olanzapine is ascribed by the literature to blocking of the dopamine $D_2$ receptor and to 5-HT antagonism.

One of the main serum metabolites of olanzapine is olanzapine-4'-N-oxide II, formed by oxidation of the nitrogen at the 4-position of the piperazinyl ring. The chemical name of II is 2-methyl-4-(4-methyl-4-oxido-1-piperazinyl)-10H-thieno[2,3-b][1,5]benzodiszepine and hereinafter is referred to as olanzapine-N-oxide.

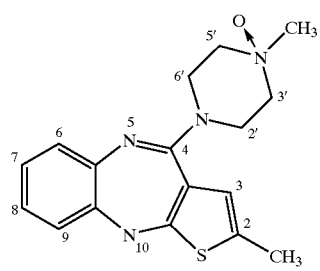

II

Because olanzapine is oxidized to olanzapine-N-oxide in the liver by P450 enzymes, drug-drug interactions arise from the concomitant administration of other drugs that stimulate or inhibit P450 or rely on P450 enzymes for their disposition. The human liver flavin-containing monooxygenase (FMO3) is involved in the metabolism of olanzapine-N-oxide. Exemplary drugs metabolized by the FMO3 enzyme include cimetidine and tamoxifen.

It is therefore desirable to find a compound with the advantages of olanzapine which would provide a more predictable dosage regimen in the patient population and that would decrease the chances for drug-drug interaction.

SUMMARY OF THE INVENTION

The present invention relates to use of olanzapine-N-oxide for treating psychosis, acute mania, mild anxiety states, anxiety disorders, schizophrenia, bipolar disorder, nautistic disorder, attention deficit hyperactivity disorder ("ADHD"), excessive aggression, substance abuse, depressive signs and symptoms, tic disorder, functional bowel disorder and fungal dermatitis. It provides this effective treatment while exhibiting fewer or less severe adverse effects than olanzapine, a lessened liability toward drug-drug interactions than olanzapine and a more predictable dosing regimen than olanzapine.

The invention also relates to pharmaceutical compositions comprising olanzapine-N-oxide. In one embodiment, said pharmaceutical compositions comprise solid unit dosage forms such as tablets or capsules, containing olanzapine-N-oxide.

DETAILED DESCRIPTION OF THE INVENTION

The active compound of the compositions and methods of the present invention is olanzapine-N-oxide. It may be prepared as described by Calligaro et al., [Biorg. & Med. Chem. Letters, 25–30, (1997)], the disclosure of which is incorporated herein by reference. Calligaro concludes that the "data demonstrate that all metabolites are significantly less active than olanzapine. It is therefore unlikely that the activity of these agents contributes to the overall pharmacological profile of the parent compound." Galatsis [Annual Reports in Medicinal Chemistry 32, 313, (1997)] also states that olanzapine's "ten metabolic products are inactive." Kando et al. [The Annals of Pharmacotherapy, 31, 1325–1334, (1997)] report that the metabolites "lack antipsychotic activity at the concentrations that have been observed."

It has now been discovered that olanzapine-N-oxide is a superior agent for treating psychoses such as acute mania and schizophrenia, mild anxiety states, anxiety disorders, bipolar disorder, autistic disorder, excessive aggression, attention deficit hyperactivity disorder ("ADHD"), substance abuse, depressive signs and symptoms, tic disorder, functional bowel disorder and fungal dermatitis. In particular, the methods and compositions of the present invention may be used to treat humans suffering from such conditions. Olanzapine-N-oxide provides this effective treatment while exhibiting fewer or less severe adverse effects than olanzapine, a lessened liability toward drug-drug interactions than olanzapine and a more predictable dosing regimen than olanzapine.

Adverse effects of olanzapine include postural hypotension, constipation, dry mouth, weight gain, dizziness, fast heart beat, personality disorder and akathisia. Other side effects of olanzapine include tachycardia, irregular pulse, diaphoresis, cardiac dysrhythmia, flu syndrome, nausea, vomiting, hematuria, metrorrhagia, urinary. incontinence, abdominal pain, premenstrual syndrome, somnolence, agitation, insomnia, nervousness, headache, dyspnea, tremors, myoglobinuria (rhabdomyolysis), drug-induced Parkinsonism, amblyopia, and asthenia.

The present invention encompasses a method of treating psychosis which comprises administering to a human in need of such therapy, an amount of olanzapine-N-oxide or a pharmaceutically acceptable salt thereof, said amount being sufficient to alleviate the symptoms of the psychotic condition. Psychotic conditions of particular interest in humans include, but are not limited to, ADHD, schizophrenia and acute mania.

The present invention also encompasses an oral composition which comprises a pharmaceutically acceptable carrier for oral administration and a therapeutically effective amount of olanzapine-N-oxide or a pharmaceutically acceptable salt thereof. Preferably the composition is in the form of a tablet or capsule, and the amount of olanzapine-N-oxide in the tablet or capsule is preferably about 1 to 150 mg.

A pharmaceutical composition of the present invention may also contain a therapeutically effective amount of a selective serotonin reuptake inhibitor in addition to a therapeutically effective amount of olanzapine-N-oxide or a pharmaceutically acceptable salt thereof, and a pharmaceutically acceptable carrier for oral administration. Selective serotonin reuptake inhibitors include, but are not limited to paroxetine (PAXIL®), fluoxetine (PROZAC®), sertaline (ZOLOFT®), fluvoxamine (LUVOX®), venlafaxine (EFFEXOR®), and nefazodone (SERZONE®), as well as any optically pure isomers or metabolites of any of these compounds.

The present invention further encompasses a method of treating bipolar disorder, anxiety disorder, tic disorder, autistic disorder, excessive aggression, ADHD, substance abuse, and signs and symptoms of depression and of treating conditions caused or contributed to by any of these. The method comprises administering to a human in need of such therapy, an amount of olanzapine-N-oxide or a pharmaceutically acceptable salt thereof, said amount being sufficient to alleviate the symptoms of the particular condition.

The present invention further encompasses a method of treating fungal dermatitis and functional bowel disorder. The method comprises administering to a human in need of such therapy, an amount of olanzapine-N-oxide or a pharmaceutically acceptable salt thereof, said amount being sufficient to alleviate the symptoms of the particular condition.

Utilizing olanzapine-N-oxide results in enhanced dosage predictability and an improved therapeutic index. In particular, olanzapine-N-oxide exhibits less potential for drug-drug interaction than does olanzapine, where flavin-containing monooxygenase inhibitors or inducers are coadministered. Olanzapine-N-oxide may also be used to treat various conditions or disorders while minimizing or avoiding adverse cardiac events associated with administration of olanzapine. Furthermore, olanzapine-N-oxide can be administered to treat various conditions or disorders while minimizing or avoiding impact on hepatic function (e.g., liver enzyme abnormalities).

The term "psychotic condition" as used herein means pathologic psychological conditions which are psychoses or may be associated with psychotic features. Such conditions include, but are not limited to the psychotic disorders which have been characterized in the DSM-IV-R, *Diagnostic and Statistical Manual of Mental Disorders Revised,* 4th Ed. (1994), including schizophrenia and acute mania. The DSM-IV-R was prepared by the Task Force on Nomenclature and Statistics of the American Association, and provides clear descriptions of diagnostic categories. The skilled artisan will recognize that there are alternative nomenclatures, nosologies, and classification systems for pathologic psychological conditions and that these systems evolve with medical scientific progress.

The term "bipolar disorder" as used herein refers to a condition characterized as a Bipolar disorder, in the DSM-IV-R as category 296.xx, including both Bipolar Disorder I and Bipolar Disorder II.

The term "autistic disorder" as used herein means a condition characterized as an Autistic Disorder in the DSM-IV-R as category 299.xx, including 299.00, 299.80, and 299.10, preferably 299.00.

The term "anxiety disorder" includes, but is not limited to, obsessive-compulsive disorder, psychoactive substance anxiety disorder, post-traumatic stress disorder, generalized anxiety disorder, anxiety disorder NOS, and organic anxiety disorder.

The term "substance abuse" as used herein means the undesired physical and/or psychological dependence on a drug. The term refers to dependence on a substance such as cocaine, psychedelic agents, marijuana, amphetamines, hallucinogen, phencyclidine, benzodiazepines, alcohol and nicotine.

The term "attention deficit hyperactivity disorder and "ADHD" as used herein mean a condition or disorder characterized by a persistent pattern of inattention, hyperactivity, impulsivity, or any combination thereof.

The term "excessive aggression" as used herein refers to a condition characterized by aggression that is so excessive that it interferes with the individual's daily functions, relationships, and may threaten the safety of the individual, for example in a situation in which violent suicide is contemplated. The excessive aggression which may be treated using the method claimed herein is independent of a psychotic condition and not directly related to the consumption of a drug or other substance.

A tic is a sudden, rapid recurrent, nonrhythmic, stereotyped motor movement or vocalization, experienced as irresistible but suppressible for varying lengths of time. Common simple motor tics include eye blinking, neck jerking, shoulder shrugging, facial grimacing, and coughing. Common simple vocal tics include throat clearing, grunting, sniffing, snorting, and barking. Common complex motor tics include facial gestures, grooming behaviors, jumping, touching, stamping, and smelling an object. Common complex vocal tics include repeating words or phrases out of context, coprolalia (use of socially unacceptable words, frequently obscene) palilalia (repeating one's own sounds or words), and echolalia(repeating the last heard sound, word or phrase). The term "tic disorder" as used herein means includes tic disorders featuring one or more motor tics and one or more tic and more vocal tics, and vocal tics. Examples include Transient Tic Disorder, Tourette's Disorder, Chronic Vocal Tic Disorder, and Tic Disorder not otherwise specified as described by DSM-IV-R.

The term "functional bowel disorder" refers to a functional gastrointestinal disorder manifested by (1) abdominal pain or (2) symptoms of disturbed defecation (urgency, straining, feeling of incomplete evacuation, altered stool form [consistency] and altered bowel frequency/timing) or (3) bloating (distension) or any combination thereof. The term "functional bowel disorder" includes but is not limited to irritable bowel syndrome, hypermotility, ichlasia, hypertonic lower esophogeal sphinchter, tachygastria, constipation, and hypermotility associated with irritable bowel syndrome.

The term "treating" as used herein includes prophylaxis of the named condition or amelioration or elimination of the condition once it has been established.

The magnitude of a prophylactic or therapeutic dose of olanzapine-N-oxide in the acute or chronic management of disease will vary with the severity of the condition to be treated and the route of administration. The dose and perhaps the dose frequency will also vary according to the age, body weight and response of the individual patient. In general, the total daily dose range for olanzapine-N-oxide for the conditions described herein is from about 1 to 150 mg in single or divided doses. In managing the patient, the therapy should be initiated at a lower dose, perhaps at about 1 mg and increased to a desired dose depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The relative activity, potency and specificity of olanzapine-N-oxide can be determined by a pharmacological study in animals according to the method of Nyberg et al. [*Psychopharmacology* 119, 345–348 (1995)]. The test provides an estimate of relative activity, potency and, through a measure of specificity, an estimate of therapeutic index. Other animal studies which may be used include, but are not limited to, studies involving conditioned avoidance, apomorphine induced climbing, and blockade of 5-hydroxy-tryptophan-induced head twitching. Although the differential metabolism among patient populations can be determined by a clinical study in humans, less expensive and time-consuming substitutes are provided by the methods of Kerr et al. [*Biochem. Pharmacol.* 47, 1969–1979 (1994)] and Karam et al. [*Drug Metab. Dispos.* 24, 1081–1087 (1996)]. Similarly, the potential for drug-drug interactions may be assessed clinically according to the methods of Leach et al. [*Epilepsia* 37, 1100–1106 (1996)] or in vitro according to the methods of Kerr et al.[op. cit.] and Turner and Renton [*Can. J. Physiol. Pharmacol.* 67, 582–586 (1989)]. In addition, the relative activity, potency and specificity of olanzapine-N-oxide may be tested using various in vitro receptor assays, including but not limited to assays involving dopamine receptors, serotonin receptors, adrenergic receptors, and muscarinic receptors.

Any suitable route of administration may be employed for providing the patient with an effective dosage of olanzapine-N-oxide. Rectal, oral, parenteral (subcutaneous, intramuscular, intravenous), transdermal, and like forms of administration are possible, but oral administration is preferred. Oral dosage forms include tablets, troches, dispersions, suspensions, solutions, capsules, soft elastic gelatin capsules, and the like.

The pharmaceutical compositions of the present invention comprise olanzapine-N-oxide as the active ingredient, or a pharmaceutically acceptable salt thereof, and may also contain a pharmaceutically acceptable carrier, and optionally, other therapeutic ingredients. In a preferred embodiment, pharmaceutical compositions of the present invention comprise olanzapine-N-oxide in combination with a selective serotonin reuptake inhibitor.

The terms "pharmaceutically acceptable salts" or "a pharmaceutically acceptable salt thereof" refer to salts prepared from pharmaceutically acceptable non-toxic acids. Since the compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Oral dosage forms suitable for olanzapine-N-oxide are described in U.S. Pat. Nos. 5, 229,382 and 5, 605,897 and in PCT application W097/11700, the disclosures of which are incorporated herein by reference.

In addition to the common dosage forms set out above, the compounds of the present invention may also be administered by controlled release formulations, which are well known in the art. Compositions suitable for rectal administration are described in European Application 645140, the disclosure of which is incorporated herein by reference.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet or capsule contains about 1 mg to about 150 mg of the active ingredient.

An enteric coating, such as the polyacrylate Eudragit L® and Eudragit S® series, is applied, preferably with an aqueous dispersion of the coating polymer. Tablets of other strengths may be prepared by altering the ratio of active ingredient to the excipients or to the final weight of the tablet.

In another embodiment, pharmaceutical compositions of the present invention suitable for oral administration may be formulated in a soft elastic gelatin capsule unit dosage form using conventional methods (see, e.g., Ebert, Pharm. Tech, 1(5):44–50(1977). Soft elastic gelatin capsules have a soft, globular, gelatin shell somewhat thicker than that of hard gelatin capsules, wherein a gelatin is plasticized by the addition of glycerin, sorbitol, or a similar polyol. The hardness of the capsule shell may be changed by varying the type of gelatin and the amounts of plasticizer and water. The soft gelatin shells may contain a preservative to prevent the growth of fungi, such as methyl- and propylparabens and sorbic acid. The active ingredient may be dissolved or suspended in a suitable liquid vehicle or carrier, such as vegetable or mineral oils, glycols such as polyethylene glycol and propylene glycol, triglycerides, sufactants such as polysorbates, or a combination thereof.

The invention is further defined by reference to the following examples describing in detail the preparation of the compositions of the present invention, as well as their utility. It will be apparent to those skilled in the art that many modifications, both to materials and methods, may be practiced without departing from the invention.

EXAMPLES

Example 1—20 mg Tablets

| Composition per tablet: | |
|---|---|
| olanzapine-N-oxide | 20 mg |
| croscarmellose | 60 mg |
| colloidal silicon dioxide | 8 mg |
| magnesium stearate | 1 mg |
| microcrystalline cellulose | 190 mg |
| croscarmellose | 15 mg |
| talc | 10 mg |
| Total | 304 mg |

Example 1

Olanzapine-N-oxide and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

Example 2—10 mg Tablets

| Composition per unit dosage: | |
|---|---|
| olanzapine-N-oxide | 10 mg |
| pregelatinized starch | 200 mg |
| microcrystalline cellulose | 25 mg |
| povidone | 15 mg |
| croscarmellose | 10 mg |
| magnesium stearate | 3.75 mg |
| FD&C yellow #2 lake | 2.5 mg |
| Water | (5 mL) |
| Total | 266.25 mg |

Example 2

The ingredients above are mixed well in the proportions shown in a high shear mixer until uniform granules result. The mixture is tray-dried at 40° C. under vacuum until the desired consistency is reached. The granules are milled to less than 60 mesh using a screen mill and compressed into tablets.

What is claimed is:

1. A pharmaceutical composition comprising olanzapine-N-oxide, or a pharmaceutically acceptable salt thereof, and one or more pharmaceutically acceptable carriers for oral therapy in the form of a tablet or capsule.

2. A pharmaceutical composition according to claim 1, additionally comprising a therapeutically effective amount of a selective serotonin reuptake inhibitor compound, or a pharmaceutically acceptable salt thereof.

3. A pharmaceutical composition according to claim 1, additionally comprising a therapeutically effective amount of a compound selected from the group consisting of paroxetine, fluoxetine, sertaline, fluvoxamine, venlafaxine, nefazodone, and pharmaceutically acceptable salts thereof.

* * * * *